United States Patent [19]
Komiya et al.

[11] Patent Number: 5,740,226
[45] Date of Patent: Apr. 14, 1998

[54] FILM THICKNESS MEASURING AND FILM FORMING METHOD

[75] Inventors: Satoshi Komiya; Naoki Awaji; Shunji Kashiwagi, all of Kawasaki, Japan

[73] Assignee: Fujitsu Limited, Kawasaki, Japan

[21] Appl. No.: 757,622

[22] Filed: Nov. 27, 1996

[30] Foreign Application Priority Data

Nov. 30, 1995 [JP] Japan ..................... 7-312441

[51] Int. Cl.$^6$ ............................. G01N 23/201
[52] U.S. Cl. ..................... 378/70; 378/76; 378/89
[58] Field of Search ...................... 378/70, 76, 89

[56] References Cited

U.S. PATENT DOCUMENTS

| | | | |
|---|---|---|---|
| 5,003,569 | 3/1991 | Okada et al. | 378/70 |
| 5,619,548 | 4/1997 | Koppel | 378/70 |

*Primary Examiner*—David P. Porta
*Assistant Examiner*—David Vernon Bruce
*Attorney, Agent, or Firm*—Staas & Halsey

[57] ABSTRACT

A film thickness measuring method comprises the steps of measuring reflectances of X-rays on a film, extracting interference oscillations from the measured X-ray reflectances, and Fourier transforming the interference oscillations to compute a film thickness of the film, an average reflectance being given by fitting the measured X-ray reflectances to an analysis formula including a term of a product of a power function of an incident angle, which expresses attenuation of reflectances on a smooth surface of the film and an exponent function which expresses influence of roughness of the surface of the film, and a constant term expressing a background added to the product; the interference oscillations being given by using the measured X-ray reflectances and the average reflectance. The film thickness measuring method can extract interference oscillations of a reflectance curve by a method including arbitrariness and by a simple procedure.

16 Claims, 13 Drawing Sheets

FILM THICKNESS MEASURING AND FILM FORMING METHOD

BACKGROUND OF THE INVENTION

The present invention relates to a film thickness measuring method for metering reflectances of X-rays on a film to measure a thickness of the film, and a film forming method using the film thickness measuring method.

In the technical fields of oxide films, electrode metal films, wiring metal films, various thin dielectric films, metal thin films of magnetic heads of recently developed large scale semiconductor devices (LSIs), etc., thin films and multi-layer films have been laid in increasing thickness, and precision requirements of the film thickness control are increasingly stricter.

In a barrier metal of an LSI, for example, a silicon oxide film, a titanium film and a titanium nitride film are laid sequentially one on another on a silicon substrate. The titanium film and the titanium nitride film of a below 10 nm-thickness to several 10 s nm-thickness require control with a precision of some Angstroms.

The measuring technique for such film thickness control is required to have high precision, to be simple, to be able to measure in a short period of time, and to uniquely determine film thicknesses. In continuously laying a plurality of films one by one in the same film forming apparatus as used for barrier metals of LSIs and metal films of magnetic heads, it is necessary to measure film thicknesses of the films in the laid state.

On the other hand, in gate oxide films and inter-layer insulation films of low dielectric constants of LSIs it is known that the film density and surface roughness thereof much affect device characteristics. Thus, in addition to the film thickness, the film density and surface roughness can be used as indices for the film quality control.

Accordingly, for administration of fabrication steps in which films are formed, measuring techniques for quickly measuring physical amounts of thicknesses of the films, densities thereof, surface roughness thereof, etc., with high precision, are required.

The conventionally used film thickness measuring techniques will be briefly explained.

Most generally, ellipsometers, which are optical means, are used in measuring film thicknesses. Polarized light is incident on an object to be measured, and a thickness of the film and a refractivity are measured based on deflections of the reflected light.

The ellipsometers, however, can be used only for materials through which light can pass, such as silicon oxide films, and cannot be used in measuring opaque films, such as barrier metals of LSIs and metal films of magnetic heads.

Furthermore, ellipsometers cannot be used for very thin films below 10 nm-thickness, such as gate oxide films of 64 MB DRAMs, even though the films are silicon oxide films, because the measuring precision is abruptly deteriorated for such very thin films.

In addition, the ellipsometer gives a film thickness on the assumption of a uniform film density. Actually, however, films of even the same material generally have different film densities depending on film forming methods, film forming conditions and film thicknesses. For example, in the case of thin silicon oxide films, they have much different film densities depending on film forming methods and film forming conditions. Accordingly, the ellipsometers cannot measure film thicknesses with high precision.

As other conventional film thickness measuring methods, X-ray fluorescence analysis, RBS (Rutherford Backscattering Spectrometry), AES (Auger Electron Spectroscopy), XPS (X-ray Photoelectron Spectroscopy), SIMS (Secondary Ion Mass Spectrometry), reflectance spectrometry, etc., are known.

In the above-mentioned X-ray fluorescence analysis, X-ray fluorescence emitted from a sample when X-rays are irradiated onto the sample is measured, and based on an intensity of the X-ray fluorescence, the amounts of elements contained in the sample are determined, and the amounts are converted into a film thickness.

In X-ray fluorescence analysis, amounts of elements alone are measured, and a resultant film thickness is a converted film thickness and is not always an actual film thickness. X-ray fluorescence analysis is not suitable for measuring multiple layers, such as layers of Ti (titanium) and TiN (titanium nitride).

In RBS, light ions of high energy are irradiated onto a sample, and an energy distribution of reward scattered light ions is analyzed to measure the film thickness of the sample.

In RBS, it is difficult to separate the energy of ions scattered rearward, and accordingly it is difficult for the RBS technique to evaluate multiple layers of elements having similar atomic masses. In addition, the RBS apparatus itself is expensive.

In measuring a film thickness of a sample by AES and XPS, the surface of the sample is sputtered with ions of, e.g., Ar for AES and XPS analysis whereby a depth-wise composition of the sample is studied, and the composition is converted into a film thickness. In measuring the film thickness of a sample by SIMS, mass analysis of secondary ions generated by irradiating ions is conducted to study the depth-wise composition of the sample, and the composition is converted into a film thickness.

The above-mentioned film thickness measuring methods of AES, XPS and SIMS are the so-called destructive inspection methods which analyze samples by sputtering the surfaces of the samples. Accordingly, these film thickness measuring methods cannot inspect products intended for actual use themselves. In addition, the sputtering processes are complicated.

In contrast to these film thickness measuring methods, X-ray reflectance spectrometry, in which X-rays are irradiated onto a sample and a film thickness of the sample is measured based on interference of the X-rays in the sample, is non-destructive and has good precision with an about 1 nm resolving power, and can evaluate film thicknesses of metal films, silicon oxide films, silicon nitride films, etc. Thus X-ray reflectance spectrometry is preferable as a method for measuring a thin film thickness. Especially advantageous is the Fourier method, in which Fourier transform interference fringes occurring in X-ray reflectances are Fourier transformed to thereby evaluate a film thickness, which can quickly and uniquely measure a film thickness.

Next, the film thickness measuring method by the conventional X-ray reflectance spectrometry using the Fourier method will be explained.

First, X-rays are irradiated onto a sample at different incident angles to thereby obtain a curve R having interference fringes.

Then, to extract interference oscillations of the curve R, an average reflectance curve $R_{ave}$ is given based on the curve R, and the average reflectance curve $R_{ave}$ is subtracted from the curve R. Thus, an oscillation component curve $\Delta(\Theta)$ including the interference oscillation alone can be given.

Subsequently, the oscillation component curve Δ(Θ) is Fourier transformed, and a relationship F(d) between Fourier coefficients F and film thicknesses d is given. The position of a peak of the thus given curve corresponds to the thickness of a film formed on the surface of a sample, and a film thickness can be uniquely determined by measuring the peak position of the curve.

In the above-described film thickness measuring process, to give a more accurate film thickness, how the average reflectance curve $R_{ave}$ is determined is important. Conventionally, the following methods have been used:

(1) data of a curve R are repeatedly averaged to give an average reflectance curve $R_{ave}$;

(2) a range is set on a curve R, and an average reflectance curve $R_{ave}$ is given by polynominal approximation;

(3) points of values near an average based on a curve R, and the points are interpolated by a spline curve; and (4) a theoretical formula of reflectances of a singly-layer sample of constituent elements alone of a thin film or a substrate is fitted to measured data to give an average reflectance curve $R_{ave}$.

The film thickness measuring method using the above-described X-ray reflectance spectrometry, however, has the characteristic that an X-ray reflectance curve R itself abruptly decreases near a total reflection critical angle, which has made it difficult to give a suitable average reflectance curve $R_{ave}$. That is, the above-described method (1) has the possibility that averaging a curve R may average the characteristics thereof themselves also. Times for the average are arbitrary, and there is a risk that the arbitrariness could be reflected in the measured film thicknesses.

The above-described methods (2) and (3) suffer from having the setting ranges and selected conditions arbitrarily selected, and also have the risk that interference oscillations are absorbed.

The above-described method (4) can give correct function forms of reflectances, but it is necessary to give densities, refractive indexes, etc., in giving the reflectances, which makes the operation of the method complicated and less universal. In measuring a film thickness of a multi-layer film, the method suffers from arbitrariness as to which film elements are used as the reference.

On the other hand, the only other conventional method for measuring a density of a film is a classic one in which a film density is calculated based on measured weights. That is, a weight and a film thickness are measured after a film to be measured is formed, then the film alone is chemically etched, and again a weight is measured. A weight of the film itself is calculated based on a weight difference after the film is etched off. A volume is separately calculated based on the film thickness and an area, and a film density is computed based on the weight of the film itself.

This conventional film density measuring method is applicable only to materials whose films can be chemically etched off. Measuring precision is much deteriorated on thin films. The measurement takes too much labor and is impractical. For these reasons and others, it is impossible to use the film density in administration of film forming steps.

As detailed above, the conventional methods are not established film thickness measuring methods which can meet the strict precision requirements of the recently developed film thickness control. A film thickness measuring method which is applicable to such film forming processes is required.

The film density and surface roughness as well as the film thickness are important indices for film quality control, thus a method for measuring the film density and the surface roughness non-destructively and with high precision is required.

SUMMARY OF THE INVENTION

An object of the present invention is to provide a film thickness measuring method which can measure a film thickness simply, with high precision and in a short period of time, and which can uniquely determine the film thickness.

Another object of the present invention is to provide a film thickness measuring method which can measure film thicknesses of respective films of a multi-layer film in their laid state.

A further another object of the present invention is to provide a film forming method which can control film forming conditions, based on measured results given by the film thickness measuring method.

The above-described objects can be achieved by a film thickness measuring method comprising the steps of measuring reflectances of X-rays on a film, extracting interference oscillations from the measured X-ray reflectances, and Fourier transforming the interference oscillations to compute a film thickness of the film, an average reflectance being given by fitting the measured X-ray reflectances to an analysis formula including a term of a product of a power function of an incident angle, which expresses attenuation of reflectances on a smooth surface of the film, and an exponent function which expresses influence of roughness of the surface of the film, and a constant term expressing a background added to the product, the interference oscillations being extracted by using the measured X-ray reflectances and the average reflectance. Characteristics of the reflectances are incorporated into the analysis formula, whereby degrees of freedom which have been arbitrarily set can be unarbitrarily limited. The analysis formula can be universally used for films of various structures with high precision. The measurement can be quicker.

In the above-described film thickness measuring method it is preferred that the analysis formula is expressed by:

$$I_0(\Theta-\Theta_0)^{-4} \cdot \exp[-(4\pi\sigma/\Lambda \cdot \sin \Theta)^2]+B_0$$

where $I_0$ represents an intensity; $\Theta$, an incident angle of X-rays; $\Theta_0$, an origin offset value for the incident angle $\Theta$; $\sigma$, a root mean square of roughness of the surface of the film; $\Lambda$, a wavelength of the X-rays; and $B_0$, a background constant.

In the above-described film thickness measuring method it is preferred that the roughness of the surface of the film is evaluated based on the root mean square of the roughness of the surface of the film given by fitting the reflectances to the analysis formula. The roughness of the surface of the film can be evaluated by a root mean squares of the roughness given by fitting an average reflectance to the analysis formula.

In the above-described film thickness measuring method it is referred that the interference oscillation is given by dividing the measured X-ray reflectances by the average reflectance.

In the above-described film thickness measuring method it is preferred that the film is a multi-layer film including two or more layers, and the film thickness is measured by setting incident angles corresponding to positions of layers of the multi-layer film, which are to be measured so that the incident angle is smaller for a layer located on an outer side of the surface of the multi-layer film, and the incident angle is larger for a layer located on an inner side of the multi-layer film. Incident angle regions are set corresponding to purposes of the measurement, and the analysis can be made at required depths.

The above-described objects can be achieved by a method for forming a film on a substrate comprising the steps of: measuring a film thickness of the film by the above-described film thickness measuring method; and adjusting film forming conditions for the film by using the measured film thickness of the film.

The above-described objects can be achieved by a method for forming a film on a substrate comprising the steps of: measuring a film thickness of the film by the above-described film thickness measuring method; computing X-ray reflectances with the measured film thickness of the film as an initial value; giving a physical amount of at least one of film density and surface and interface roughness of the film by fitting the measured X-ray reflectances to the computed X-ray reflectances; and adjusting the film forming conditions for the film by using the physical amount of at least one of film thickness, film density and surface and interface roughness of the film.

In the above-described method for forming a film on a substrate it is possible that by using the physical amount of said at least one of film thickness, film density and surface and interface roughness of the film, at least one parameter of film forming temperature, a gas feed amount, and a gas mixing ratio is adjusted for a processing apparatus for any one of oxidation treatment, nitridation treatment, oxidation/nitridation treatment, sputtering, CVD, electron beam deposition, ion beam deposition, molecular beam deposition and liquid phase growth.

The above-described objects can be achieved by a method for etching at least a part of a film formed on a substrate comprising the steps of: measuring a film thickness of the etched film by the above-described film forming method; and adjusting etching conditions of the film by using the measured film thickness of the film.

DETAILED DESCRIPTION OF THE INVENTION

A film forming method according to a first embodiment of the present invention will be explained with reference to FIGS. 1 to 6.

Figure 1:
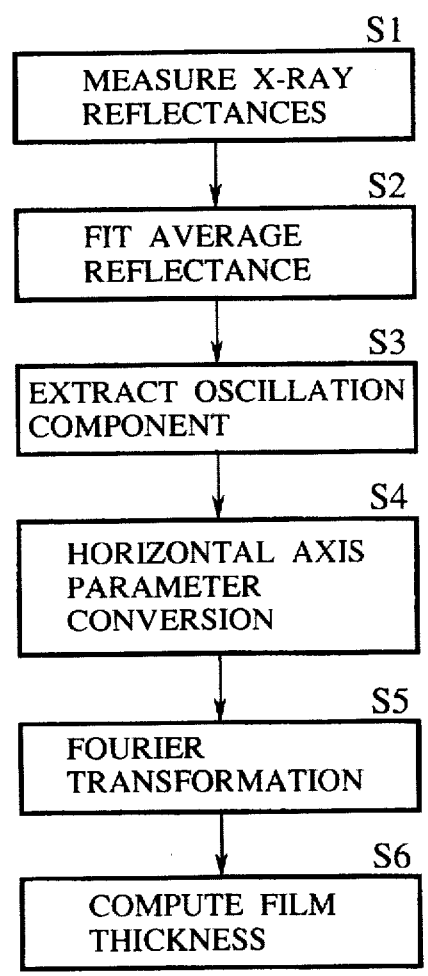
FIG. 1 is a view diagrammatically explaining the film thickness measuring method according to a first embodiment of the present invention.

FIG. 1 is a view explaining the film thickness measuring method according to the present embodiment. FIGS. 2, and FIGS. 4 to 6 are graphs of results of the measurement by the film thickness measuring method according to the present embodiment. FIG. 3 is graphs of results of the measurement by a conventional film thickness measuring method.

First, the film thickness measuring method according to the present embodiment will be briefed with reference to FIG. 1.

First, X-rays are irradiated onto the surface of a sample on which a film to be measured is formed, and X-ray reflectances are measured to give a curve R (step S1).

Then, an average reflectance curve $R_{ave}$ is obtained based on the curve R given in step S1 (step S2).

Subsequently the average reflectance curve $R_{ave}$ is subtracted from the curve R to extract an oscillation component curve $\Delta(\Theta)$, reflecting interference oscillations of the curve R (step S3).

Then, parameters of the oscillation component curve $\Delta(\Theta)$ are converted to give an oscillation component curve $\Delta(\Theta)$ (step S4).

Then, the oscillation component curve $\Delta(x)$ is Fourier transformed (step S5). A film thickness is measured based on the position of a peak of a given Fourier coefficient F(d) (step S6).

The present embodiment is characterized by the film thickness measuring method using the above-described X-ray reflectance spectrometry in which, according to the present embodiment, in giving an average reflectance curve $R_{ave}$, data are fitted by using an analysis formula having a term of a product of a power function of an incident angle, which expresses attenuation of a reflectance on a smooth sample surface, an exponent function expressing influence by a rough sample surface, and a constant term expressing a background.

The inventors of the present invention newly found that an average reflectance curve $R_{ave}$ can be fitted by the use of such an analysis formula with high precision and without introducing any arbitrary values.

Specifically, for example:

$$R = I_0 (\Theta - \Theta_0)^{-4} \exp[-(4\pi\sigma/\Lambda \cdot \sin\Theta)^2] + B_0 \tag{1}$$

can be used.

In the formula, $I_0$ represents an intensity; $\Theta$, an incident angle of X-rays; $\Theta_0$, an origin offset value for $\Theta$; $\sigma$, a root mean square (hereinafter called rms (root mean square) roughness) of a sample surface; $\Lambda$, a wavelength of the X-rays; and $B_0$, a background constant. The background constant $B_0$ includes zero. The incident angle in the specification of the present application does not mean an angle to a normal but instead means an angle formed by a sample surface and the incident X-rays.

In the present embodiment, a function $I_0(\Theta-\Theta_0)^{-4}$ is used as a power function of an incident angle, which expresses attenuation of the reflectance on a roughness-free (or smooth) sample surface. This is because a reflectance on a sample without roughness on the surface has the characteristic of decreasing proportional to $\Theta^{-4}$ for an incident angle $\Theta$ of the X-rays on the sample surface.

An exponent function expressing the influence by the sample surface roughness is: $\exp\{-(4\pi\sigma/\Lambda \cdot \sin \Theta)^2\}$. This is because when the Debye-Waller roughness is assumed with an rms roughness as $\sigma$, attenuation of a reflectance on this roughness is approximately expressed by $\exp\{-(4\pi\sigma/\Lambda \cdot \sin \Theta)^2\}$.

Accordingly, the analysis formula with reflectance characteristics incorporated therein can be given by using a term of a product of these functions, whereby the degree of freedom, which has been uncontrollable, can be correctly controlled.

This analysis formula is a monotonic decreasing function having four parameters: $I_0$, $\Theta$, $\sigma$, and $B_0$, and there is no possibility that oscillations of the curve R are absorbed in fitting an average reflectance curve.

The parameters do not contain specific constants related to specific samples, which makes the analysis function universal.

Furthermore, when a curve R is fitted by this analysis formula, information of roughness of a sample surface can be concurrently obtained based on the value of $\sigma$.

For the fitting of a curve, the method of least squares, for example, may be used.

Silicon Oxide Film: SiO$_2$

Next, data from a simulation of X-ray reflectances were analyzed by a conventional method and by the film thickness measuring method according to the present embodiment, and results of the analysis were compared.

FIG. 2 shows graphs of the results of the analysis by the film thickness measuring method according to the present embodiment, and FIG. 3 shows graphs of the results of the analysis by the conventional method.

The analysis was conducted on the results of the simulation of X-ray reflectances on ultra-thin silicon oxide film at a 5 nm-thickness and a 0.4 nm surface roughness. The curves R shown in FIGS. 2A and 3A were given based on reflectances obtained by the simulation, and thicknesses of the silicon oxide film were given by the conventional method and by the measuring method according to the present embodiment.

In the film thickness measuring method according to the present embodiment, an average reflectance curve $R_{ave}$ was fitted by the method of least squares by the use of analysis formula (1). In the conventional method of FIG. 3, the curve R was smoothed in each 100 data point regions to obtain an average reflectance curve $R_{ave}$ (step S2).

Values of the respective parameters obtained in fitting the curves to the analysis formula (1) were:

$I_0$=7.98 (8)

$\Theta_0$=0.001 deg (0 deg)

$\sigma$=0.397 nm (0.4 nm)

$B_0$=5.16 (5).

The above parenthesized values were the parameters actually used in the simulation. In the film thickness measuring method according to the present embodiment, rms roughness $\sigma$ can be given in fitting the average reflectance curve $R_{ave}$, and its value was 0.397 nm, which was within the allowable error.

Then, oscillation components of the curves R were extracted based on the curves R and on the average reflectance curves $R_{ave}$ (step S3). Oscillation component curves $\Delta(\Theta)$ were calculated according to:

$$\Delta(\Theta)=\log R(\Theta)-\log R_{ave}(\Theta) \quad (2)$$

Subsequently, horizontal axis parameter conversion of the oscillation component curves $\Delta(\Theta)$ was conducted (step S4). The parameter conversion was conducted by the use of:

$$x=\sqrt{(\Theta^2-\Theta_c^2)/\Lambda} \quad (3)$$

wherein $\Lambda$ represents a wavelength of the X-rays, and $\Theta$ represents a total reflection critical angle.

Figure 2A:
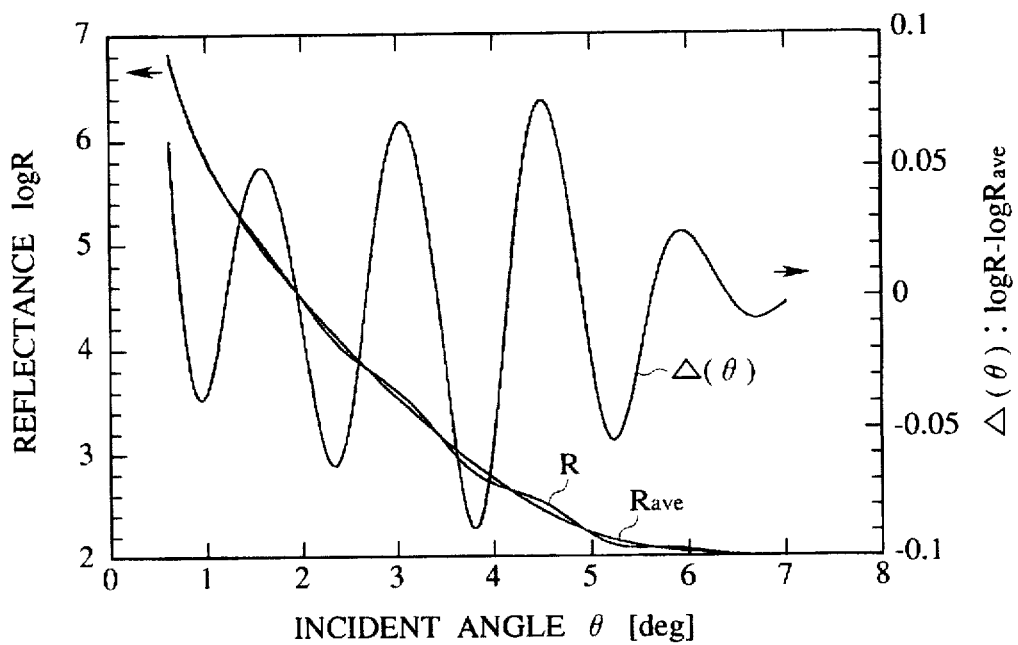
FIGS. 2A and 2B are graphs of results of analysis of a reflectance curve given by a simulation, which was made by the film thickness measuring method according to the first embodiment of the present invention.
Figure 2B:
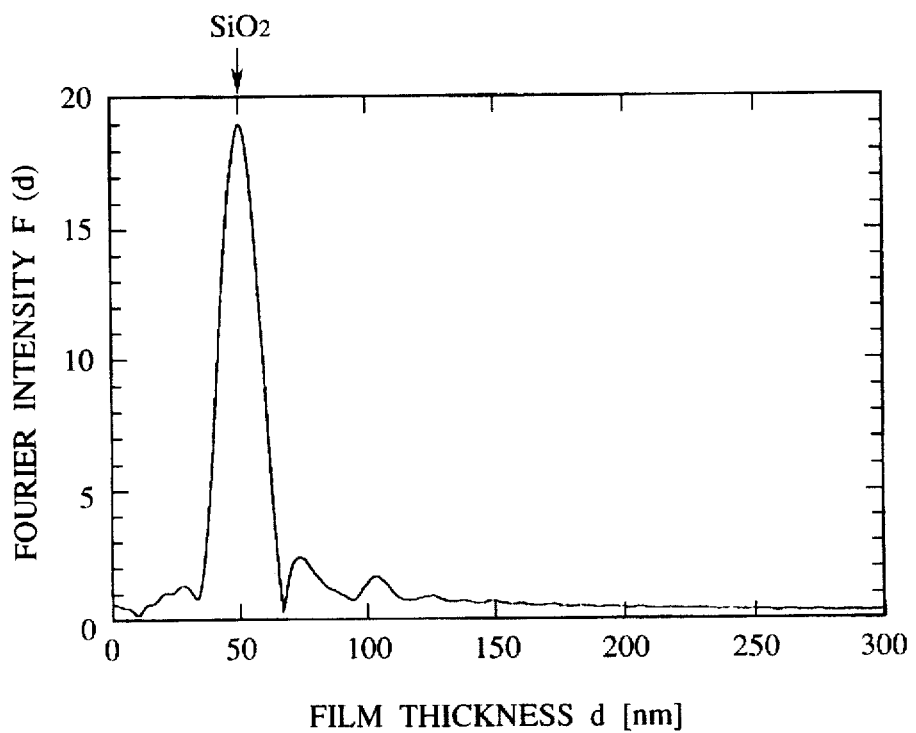
Figure 3A:
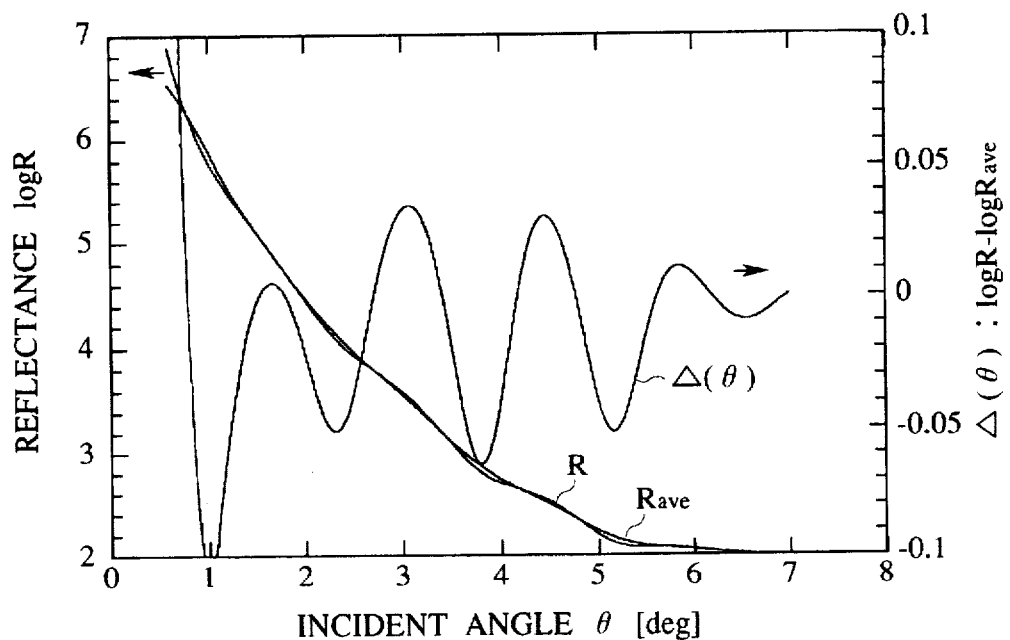
FIGS. 3A and 3B are graphs of results of analysis of the reflectance curve given by the simulation, which was made by a conventional film thickness measuring method.
Figure 3B:
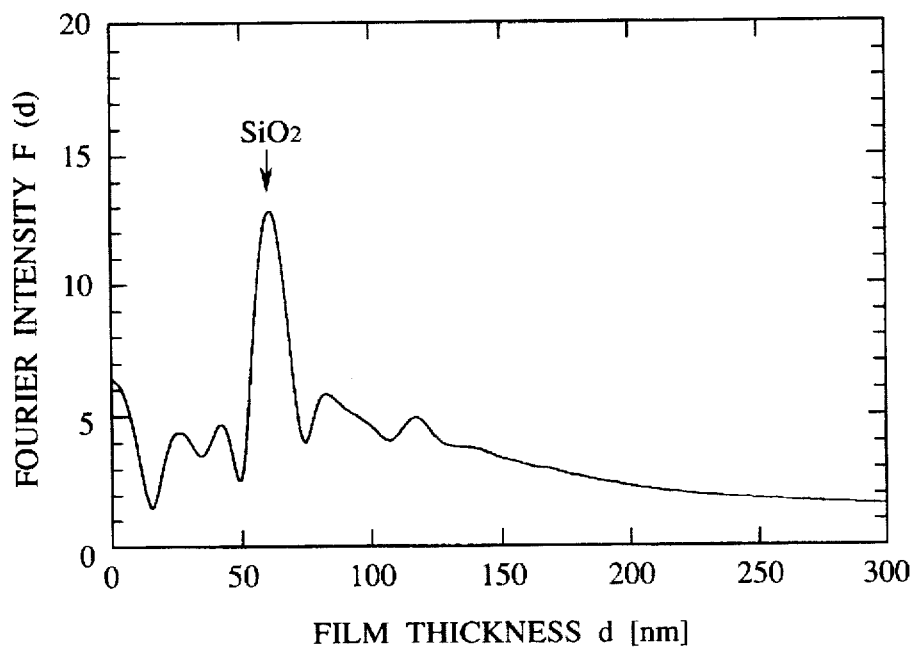

Then, the parameter-converted oscillation component curves (x) were Fourier transformed, and the Fourier coefficient F(d) shown in FIGS. 2B and 3B were given (step S5).

The positions of the thus-obtained peaks were measured to measure the film thickness of the silicon oxide film, and the result was that a film thickness given by the film thickness measuring method according to the present embodiment was 5.1 nm while a film thickness given by the conventional method was 6.1 nm, which was much deflected.

Multi-Layer Film: TiN/Ti/SiO$_2$/Si

Next, a curve R was obtained by an experiment using a sample comprising a 40.8 nm-thick silicon oxide film, a 7.7 nm-thick TiN film and a 15.6 nm-thick TiN film laid sequentially on a silicon substrate, and results of the analysis of the film by the film thickness measuring method according to the present embodiment are shown in FIGS. 4 to 6.

FIG. 4 shows the result of the analysis for all angular regions, FIG. 5 shows the results of the analysis for a 0°–2° angular region, and FIG. 6 shows the results of the analysis for a 2°–6° angular region. In the analysis average reflectance curves $R_{ave}$ were given by fitting the curves R to the analysis formula (1) by the method of least squares. Values of the respective parameters given by the analysis were:

$I_0$=8.34

$\Theta_0$=0.002 deg $\sigma$=0.387 nm $B_0$=11.06.

An rms roughness of the surface of the sample was found to be 0.387 nm.

Figure 4A:
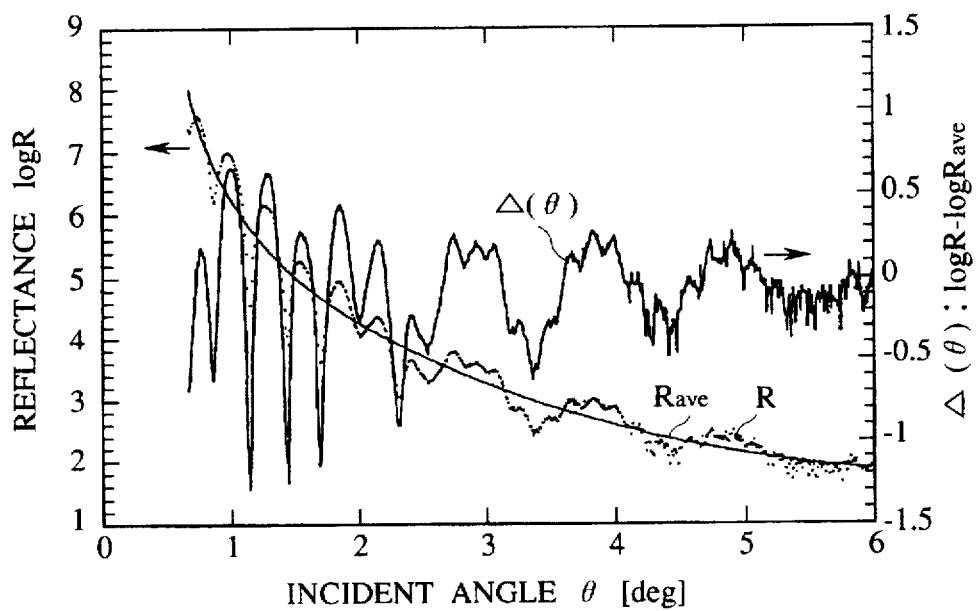
FIGS. 4A and 4B are graphs of results of the analysis of a multi-layer film (TiN/Ti/SiO$_2$/Si) by the film thickness forming method according to the first embodiment of the present invention.
Figure 5A:
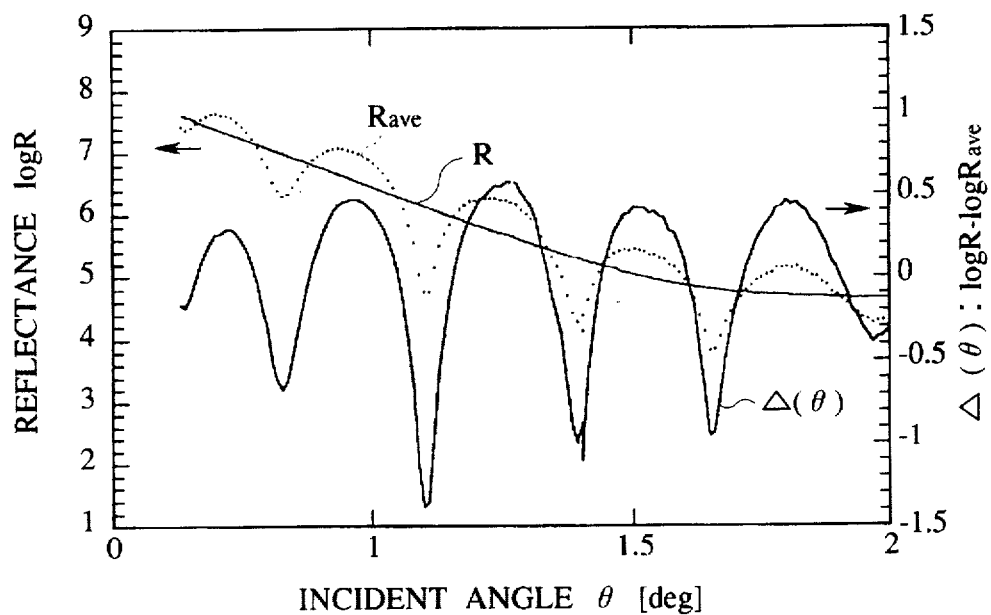
FIGS. 5A and 5B are graphs of results of the analysis which was restricted in a smaller incident angle region.
Figure 6A:
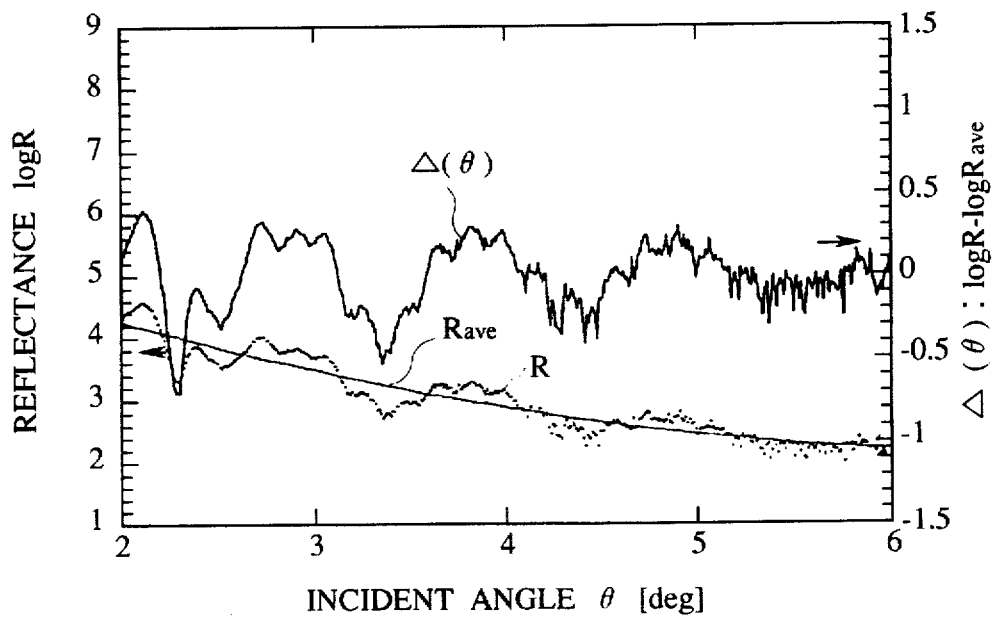
FIGS. 6A and 6B are graphs of results of the analysis which was restricted in a larger incident angle region.

As shown in FIGS. 4A, 5A and 6A, it was found that the average reflectance curves $R_{ave}$ obtained by the fitting were smooth in all the angular regions.

Based on the thus-given average reflectance curves $R_{ave}$, oscillation component curves $\Delta(x)$ were given by using formulas (2) and (3) and were Fourier transformed. The graphs of the Fourier coefficient F(d) shown in FIGS. 4B, 5B and 6B were given.

Figure 4B:
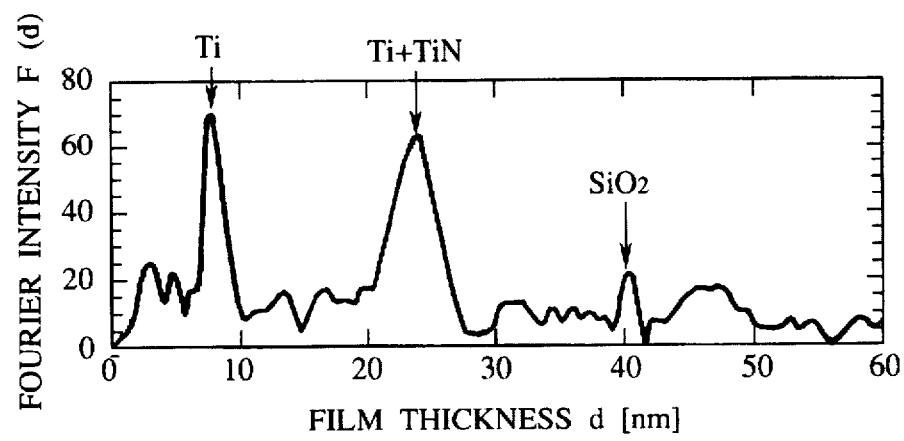

In the graph of FIG. 4B, an interference peak indicative of the Ti film, an interference peak indicative of the Ti film and the TiN film, and an interference peak indicative of the silicon oxide film were found. The positions of the peaks correspond respectively to 7.5 nm, 23.8 nm, and 40.6 nm. Accordingly a given film thickness of the Ti film was 7.5 nm, that of the TiN film was 16.3 nm, and that of the silicon oxide film was 40.6. It was found that a film thickness can be measured with a measuring precision having an about 0.05 nm allowable error by the use of the film thickness measuring method according to the present embodiment.

Figure 5B:
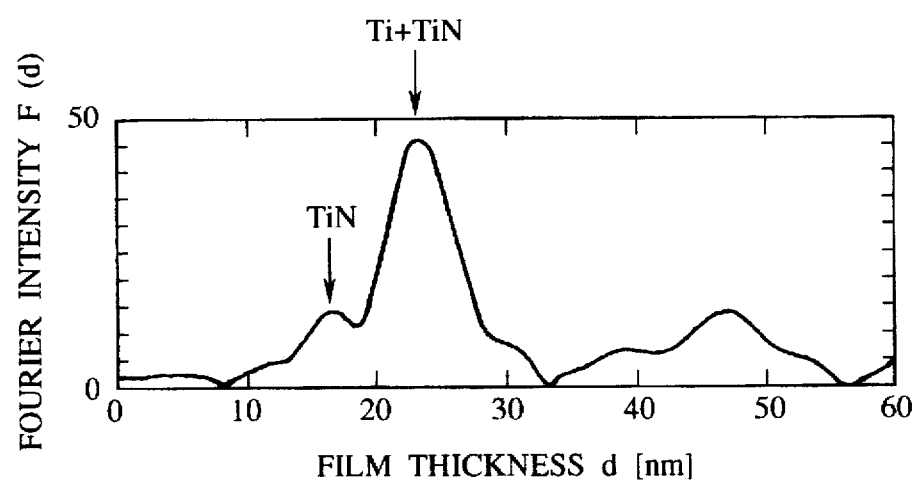

The result shown in FIG. 5B of the analysis in the small-angle region shows that interference peaks of the Ti film and the silicon oxide film disappeared, and only an interference peak of the TiN film and that of the Ti film and the TiN film were detected.

Figure 6B:
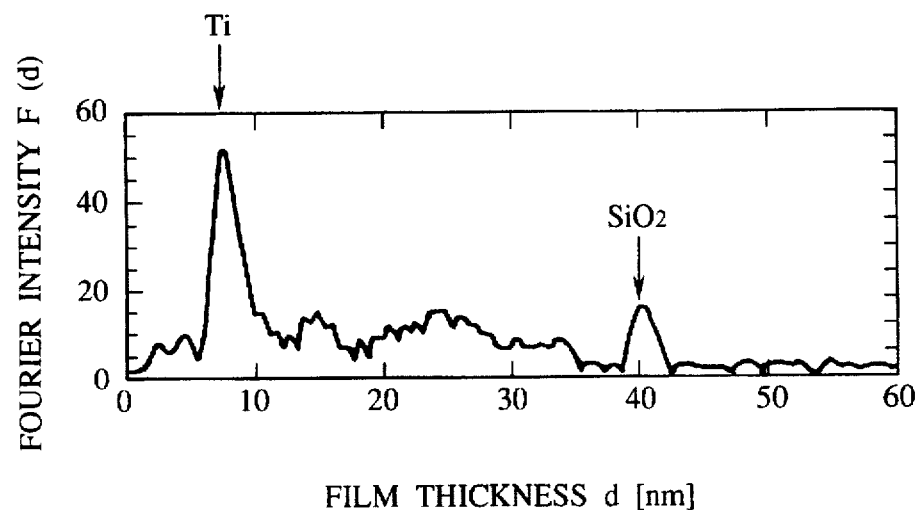

On the other hand, in the result shown in FIG. 6B of the analysis in the large-angle region, the interference peak of the TiN film disappeared, and an interference peak of the Ti film and that of the silicon oxide film were detected.

The reason why peaks vary thusly in different analysis angle regions is because X-rays can more deeply enter a sample as they have larger incident angles, and at larger incident angles, information of the sample at deeper positions can be obtained. Accordingly, the range of the angular measuring region is restricted corresponding to the measuring purpose, whereby the analysis can be conducted to a required depth. For example, when an upper film is to be measured, an analysis range can be restricted to a small-angle region, and an analysis range can restricted to a larger-angle region when a lower film is to be measured.

Gate Oxide Film: $SiO_2$

Next, a gate oxide film formed on a silicon substrate under the following conditions was analyzed by the film thickness measuring method according to the present embodiment, and the results of the analysis will be explained.

As film forming conditions, the film forming temperature was 1000° C., an atmospheric gas was oxygen (200 Torr), a thermal oxidation time was 30 minutes, and under these conditions an about 4 nm-thick gate oxide film was formed.

In measuring reflectances of X-rays, X-rays of a 1.3 Angstrom wavelength were used, and reflectances of the X-rays on the gate oxide film were measured in a range of 0°–7° for the scattering angles (twice the incident angle of the X-rays).

FIG. 7 shows results of the analysis of the gate oxide film by the film thickness measuring method according to the present embodiment. An average reflectance curve $R_{ave}$ was given by fitting a curve R to analysis formula (1) by method of least squares.

Values of the parameters given by the analysis were:

$I_0=6.93$ $\Theta_0=0.002$ deg $\sigma=0.37$ nm $B_0=10.5$.

An rms roughness of the surface of the sample was found to be 0.37 nm.

Figure 7A:
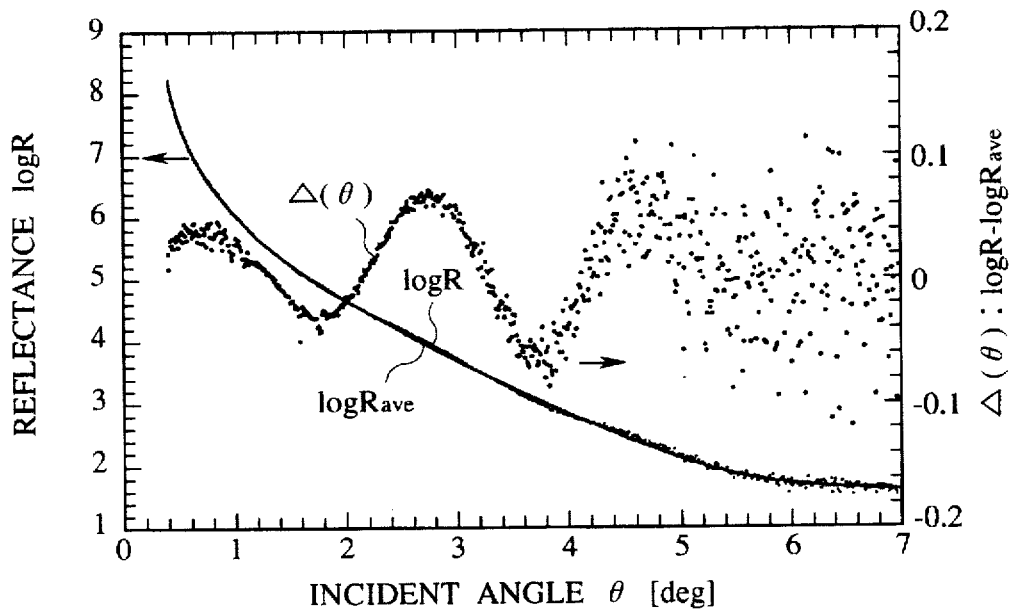
FIGS. 7A and 7B are graphs of results of the analysis of silicon oxide film by the film thickness measuring method according to the first embodiment of the present invention.

As shown in FIG. 7A, the average reflectance curve $R_{ave}$ was smooth. Based on the thus-given average reflectance curves $R_{ave}$, oscillation component curves $\Delta(x)$ were given by using formulas (2) and (3) and were Fourier transformed. The graphs of the Fourier coefficient F(d) shown in FIG. 7B was given.

Figure 7B:
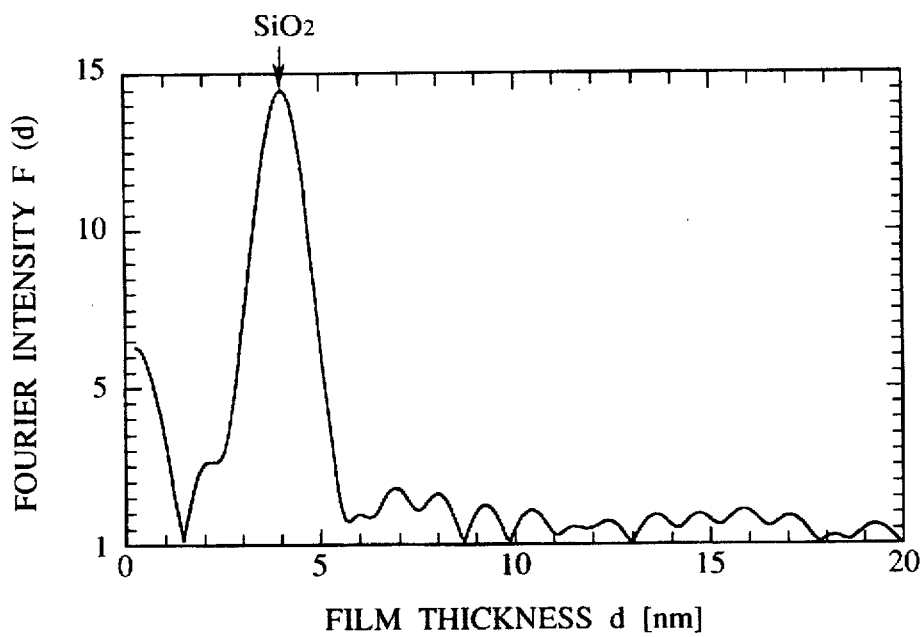

The graph shown in FIG. 7B has a clear interference peak indicative of the gate oxide film, and the position of the peak was 3.9 nm. Accordingly, a measured film thickness of the gate oxide film was 3.9 nm.

Gate oxide films for DRAMs will have an about 10 nm thickness for 64 MB DRAMs and an about 6–7 nm-thickness for 1 GB DRAMs. Conventionally, there have been no methods which can accurately and simply measure film thicknesses of these gate oxide films. Methods using the conventional ellipsometers abruptly deteriorate precision of measuring film thicknesses at below 10 nm. In contrast to this, the present embodiment can simply and accurately measure in a short period of time film thicknesses of ultra-thin films below 10 nm thick. Furthermore, based on the measured film thicknesses, it is possible to control the film forming steps.

Titanium Nitride Film: TiN (Film Thickness)

Next, titanium nitride film was formed on a silicon substrate under the following film forming conditions, and results of the analysis on the titanium nitride film are shown.

Film forming conditions of the titanium nitride film by sputtering were: titanium as the target, a 400 W RF output, nitrogen atmospheric gas, and a 10 sccm (Standard Centimeter per Minute) gas flow rate.

In measuring reflectances of X-rays, X-rays of a 1.3 Angstrom wavelength were used, and reflectances of the X-rays on the titanium nitride in a 0°–6° X-ray incident angle range were measured.

Figure 8A:
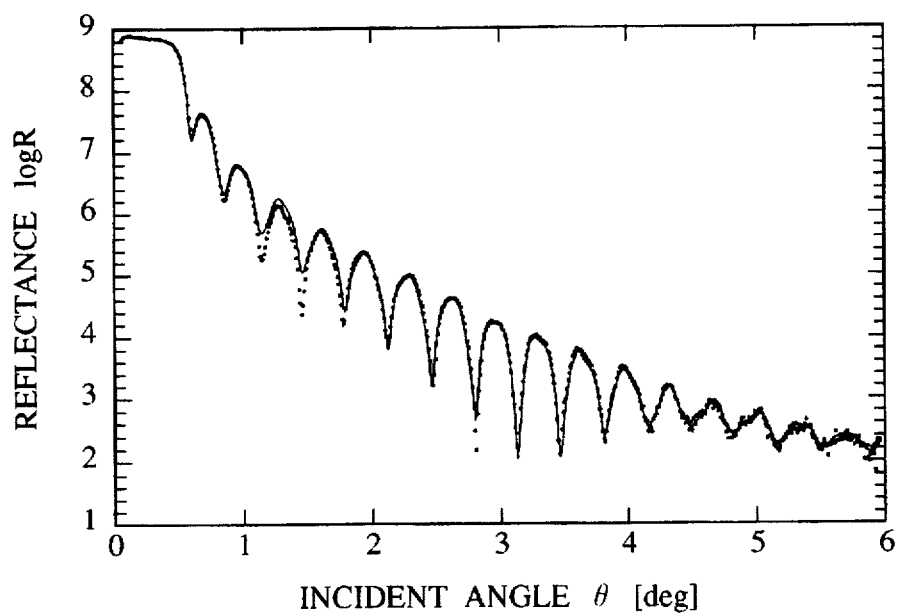
FIGS. 8A and 8B are graphs of results of the analysis of titanium nitride film by the film thickness measuring method according to the first embodiment of the present invention.

FIG. 8 shows results of the analysis by the film forming method according to the present embodiment. In the same procedure as described above, measured values of the X-ray reflectances were analyzed to give an oscillation component curve $\Delta(x)$ as shown in FIG. 8A. The oscillation component curve $\Delta(x)$ was Fourier transformed, and the graph of Fourier coefficient F(d) shown in FIG. 8 was given.

Figure 8B:
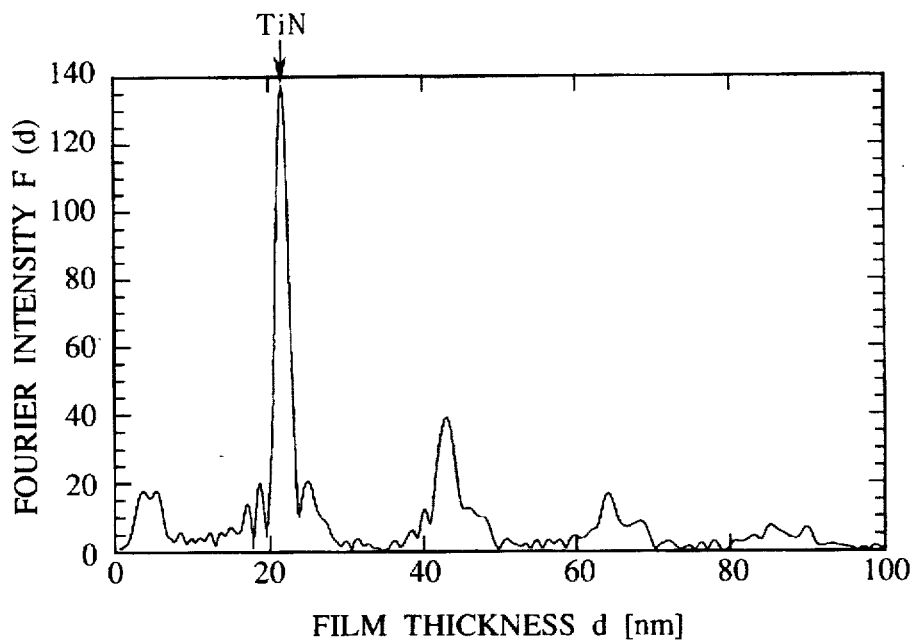

The graph of FIG. 8B has a very clear interference peak indicative of the titanium nitride film, and the position of the peak was 21.4 nm. A measured film thickness of the titanium nitride film was 21.4 nm.

The period of time the present embodiment took for the fitting analysis was as short as some minutes.

The film thickness of titanium nitride film, which is an opaque metal film, cannot be measured by ellipsometer. It is also impossible to compute, based on fluorescent X-ray intensities, the film thickness of titanium nitride film, which is a compound. Film thickness of titanium nitride film can be measured by electron microscopy, which is effective to obtain basic data, but this method takes too much labor to be used as a measuring technique for film forming control.

In addition, titanium nitride film, which is formed by sputtering, has states that subtly vary depending on forming conditions, such as RF voltages, gas flow rates, gas component ratios, etc. When films are formed in a string of film forming steps, very fine film forming control is necessary.

According to the present embodiment, film thickness can be measured simply and accurately in a short period of time. For example, films are formed on monitor substrates at the start of a string of film forming steps, and based on measured values of thicknesses of these films on the monitor substrates, subsequent film forming conditions can be finely controlled. By monitoring measured data for a long period of time, film forming conditions can be adjusted in accordance with transient changes within film forming apparatuses.

Multi-Layer Film: $TiN/Ti/SiO_2/Si$

A sample comprising a silicon oxide film, a Ti film and a TiN film sequentially laid on a silicon substrate was analyzed by the film thickness measuring method according to the present embodiment, and results of the analysis will be explained.

Figure 9:
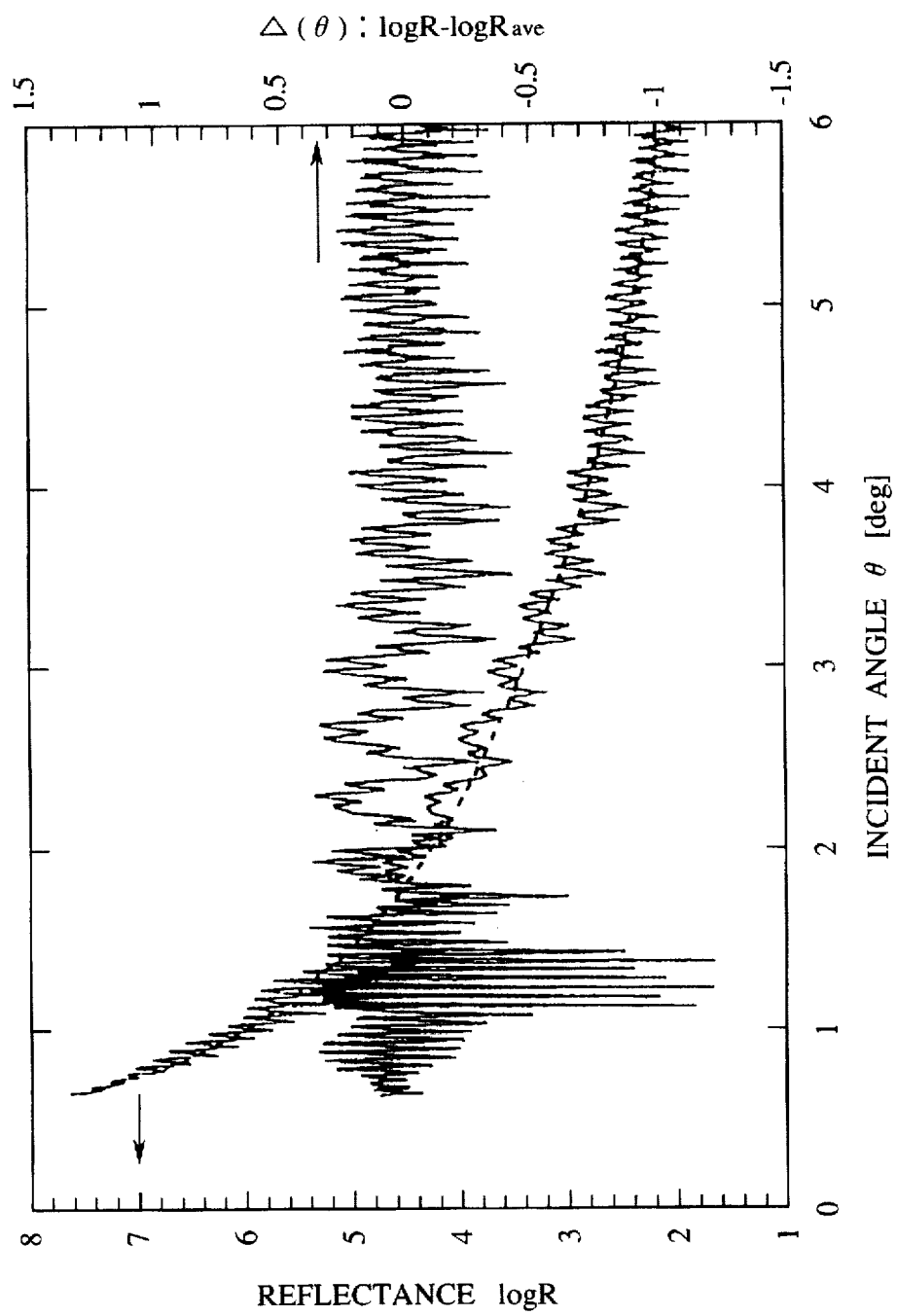
FIG. 9 is a graph of results of the analysis of a multi-layer film (TiN/Ti/SiO$_2$/Si) by the film thickness measuring method according to the first embodiment of the present invention.

FIG. 9 shows results together with the results of the analysis in angular regions divided in three. FIG. 10 shows the result of the analysis in a 0.6°–2° angular region. FIG. 11 shows the result of the analysis in a 2°–4° angular region. FIG. 12 shows the result of the analysis in a 4°–6° angular region. Average reflectance curves $R_{ave}$ were given by fitting curves R to the analysis formula (1) by the method of least squares.

Values of the parameters given by the analysis were:

$I_0=7.2$ $\Theta_0=-0.002$ deg $\sigma=1.6$ nm $B_0=15.3$.

An rms roughness of the surface of the sample was found to be 1.6 nm.

As shown in FIGS. 9A, 10A, 11A, and 12A, it was found that the average reflectance curves $R_{ave}$ obtained by the fitting were smooth in all the angular regions.

Based on the thus-given average reflectance curves $R_{ave}$, oscillation component curves $\Delta(x)$ were given by using formulas (2) and (3). Characteristics of the oscillation component curves in the respective angular regions will be explained.

Figure 10A:
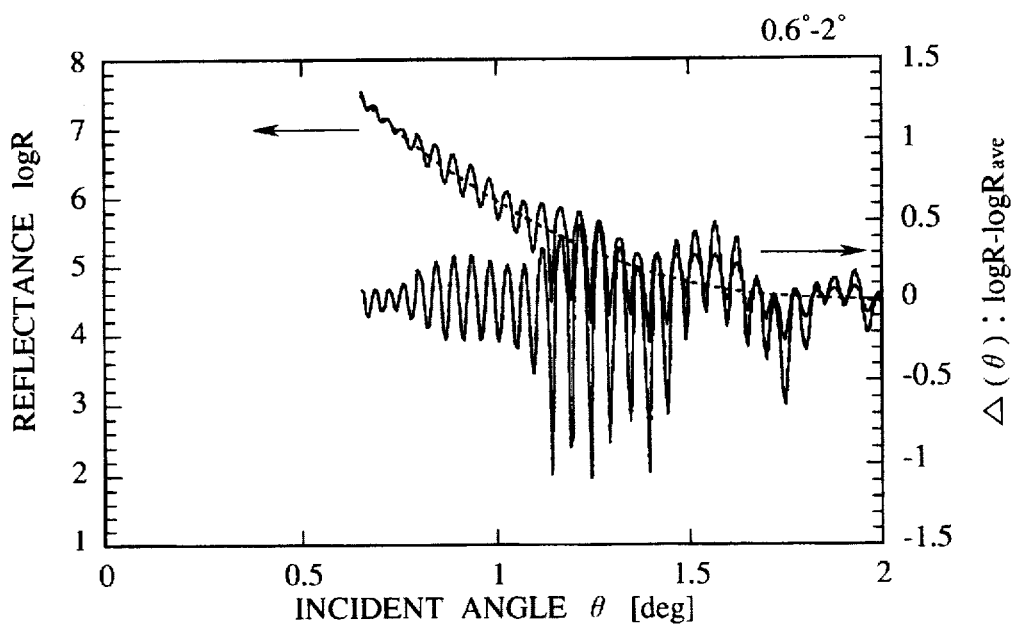
FIGS. 10A and 10B are graphs of results of the analysis with the incident angle region restricted to a 0.6°–2° range.
Figure 11A:
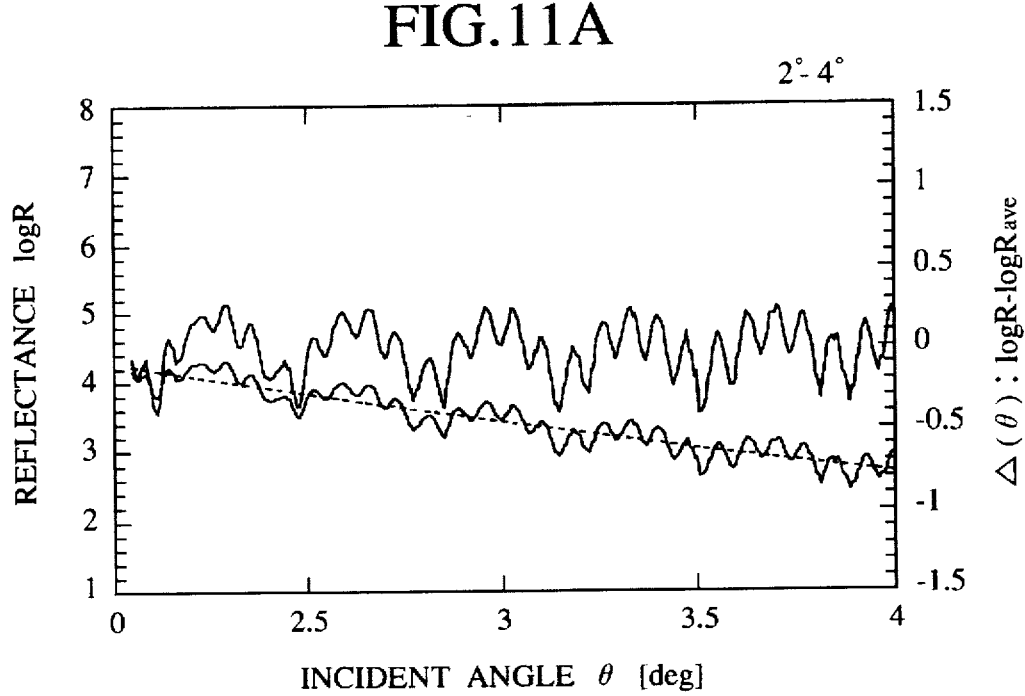
FIGS. 11A and 11B are graphs of results of the analysis with the incident angle region restricted to a 2°–4° range.
Figure 12A:
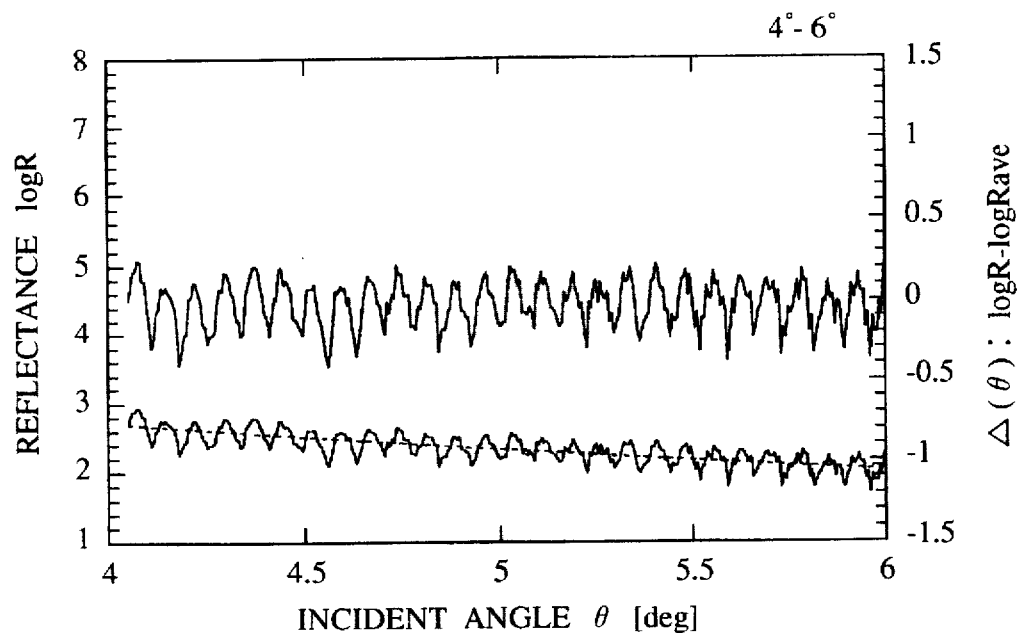
FIGS. 12A and 12B are graphs of results of the analysis with the incident angle region restricted to a 4°–6° range.

As shown in FIG. 10A, in the relatively small-angle region of 0.6°–2°, interference oscillations of the TiN film which were subjected to modulation of the Ti film, were found. As shown in FIG. 11A, in the middle-angle region of 2°–4° interference oscillations of the Ti film overlapped a short-period modulation by the $SiO_2$ film. As shown in FIG. 12A, in the relatively large-angle region, monotonous interference oscillations of the lowermost $SiO_2$ film were found.

Based on the result of analysis in the all-angle region, differences in the characteristics of the interference oscillations in the respective angle regions were understood.

Figure 10B:
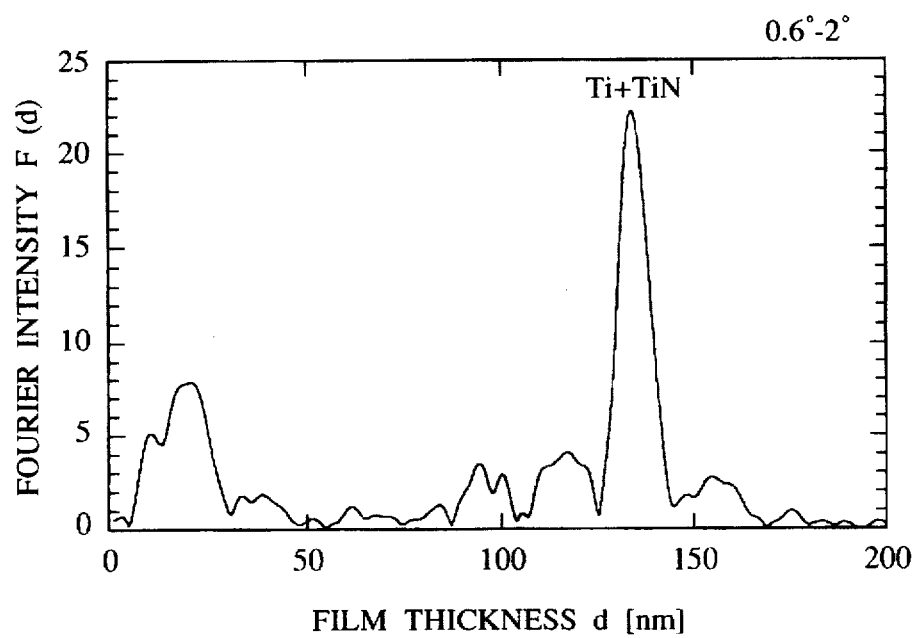
Figure 11B:
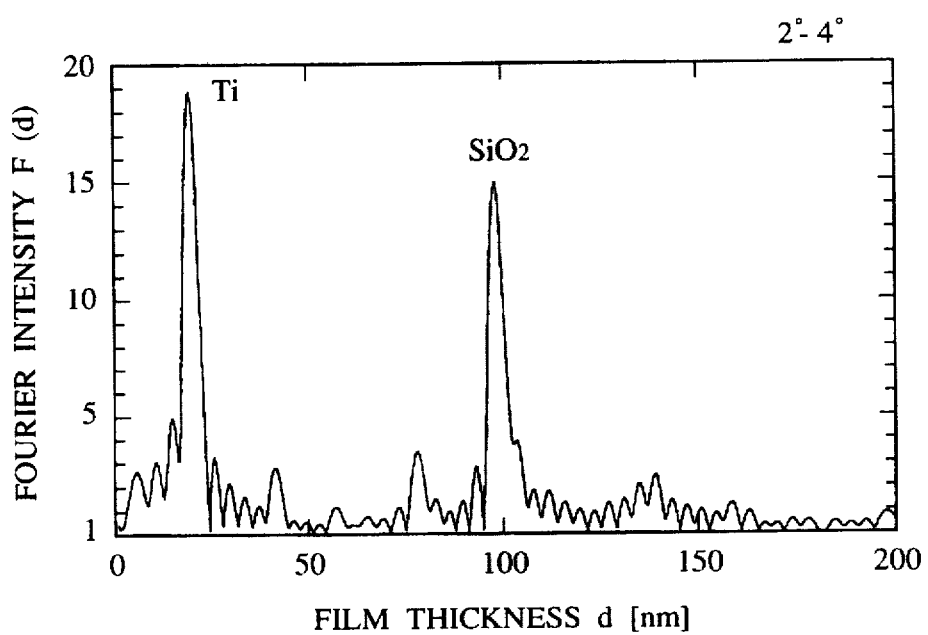
Figure 12B:
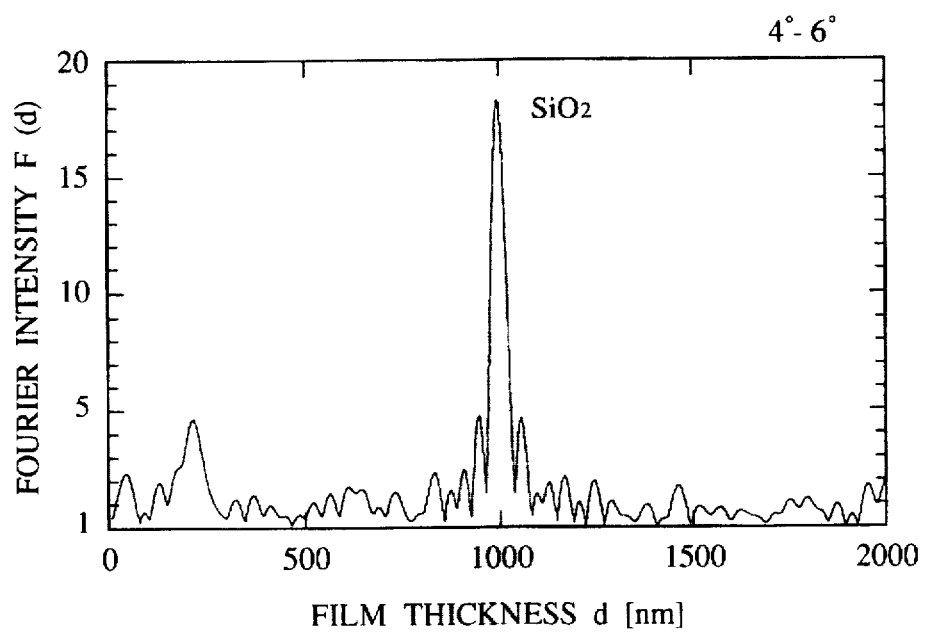
Figure 13:
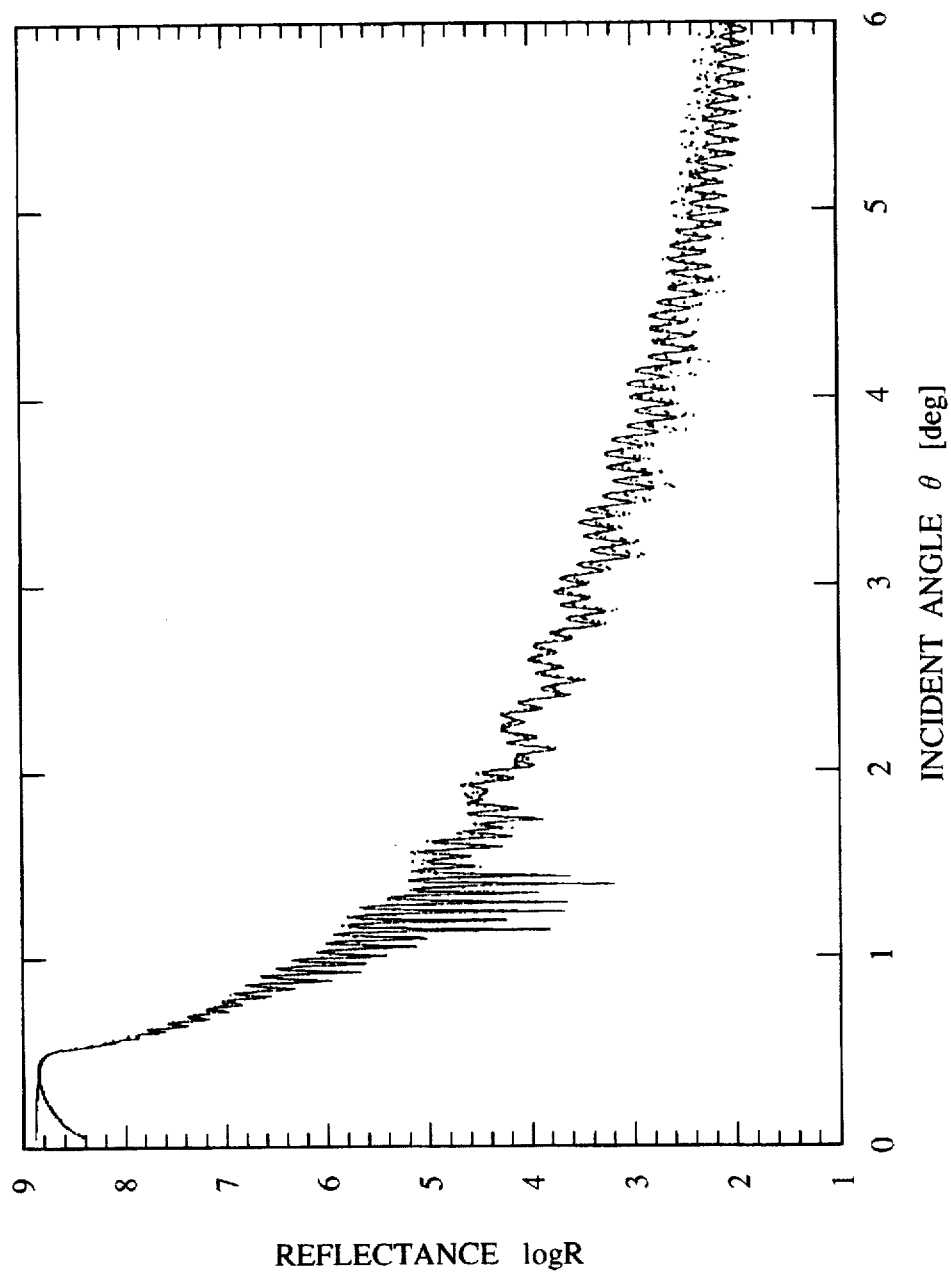
FIG. 13 is a graph of results of the analysis with the incident angle region set over all the angles of 0°–6°.

The interference oscillations of FIGS. 10A, 11A and 12A were Fourier transformed, and the graphs of Fourier coefficient F(d) shown in FIGS. 10B, 11B and 12B were obtained.

As shown in FIG. 10B, in the relatively small-angle region of 0.6°–2°, a peak corresponding to a sum of film thicknesses of the Ti film and the TiN film was found at the position of 135.2 nm. In this multi-layer film, a density difference between the Ti film and the $SiO_2$ film was large in comparison with a density difference between the Ti film and the TiN film so that the sum of the Ti film thickness and the TiN film thickness appeared in the peak. As shown in FIG. 11B, in the middle-angle region of 2°–4°, a peak corresponding to the Ti film was found at the position of 20.6 nm, and a peak corresponding to the $SiO_2$ film was clearly found at the position of 99.7 nm. No peak corresponding to the TiN film appeared. As shown in FIG. 12B, in the relatively large-angle region, a peak corresponding to the $SiO_2$ film was clearly found at 99.8 nm.

Based on analysis of these results, a film thickness of the TiN film was found to be 114.6 nm, that of the Ti film was found to be 20.6 nm, and that of the $SiO_2$ film was found to be 99.8 nm. These values agreed to, within ±1%, the accurate true film thicknesses (TiN film thickness: 115.1 nm, Ti film thickness: 20.4 nm, $SiO_2$ film thickness: 99.9 nm) given by trial-and-error fitting, assuming certain values for all the parameters, such as the film thickness, film density, roughness, etc.

For comparison, a fitting was conducted for the single region which was not divided in the three regions. As a result, the oscillation component curve $\Delta(x)$ shown in FIG. 3 was obtained. The oscillation component curve $\Delta(x)$ was Fourier transformed, and a film thickness of the TiN film was found as 117.1 nm, that of the Ti film was found as 20.4 nm, and that of the $SiO_2$ film was found as 100.3 nm.

Significant deflections from the accurate film thicknesses were thus found.

Thus, in a case of a multi-layer film including two or more layers, an incident angle region to which a layer reflects its interference oscillations can be determined when a structure (a sequence of layers) of the multi-layer structure, and materials and thicknesses of the respective films are determined. Then, when target values of film thickness of the films of the multi-layer film to be measured are known, it can be presumed based on a structure of a multi-layer film and materials thereof which angle region should be analyzed for a particular film.

In the analysis of X-ray reflectances, setting different incident angles in accordance with regions can reduce intrusion of extra oscillation components (i.e. noise), and the peaks of Fourier intensity curves after the Fourier transformation are clear, which facilitates identification of thicknesses of the films.

Usually, in respective film forming steps of forming multi-layer films, needless to say, the structure of the multi-layer films, the materials of the respective films, and the target values of the respective film thicknesses are set. Accordingly, angular regions which are optimum for multi-layer films may be kept as a data base, and the data base is used prior to actually analyzing measured values and computing film thicknesses, whereby it is possible to compute film thicknesses quickly and accurately. Also in measuring X-ray reflectances, the angular precision corresponding to film thicknesses, and the angular regions of incident angles corresponding to various purposes may be kept as a data base, whereby it is possible that the measurements are more efficient and quicker.

As a conventional film thickness measuring method for metal thin film, there is a method for computing film thickness based on X-ray fluorescence intensities, using reference samples, but this method cannot compute film thickness of multi-layer films (TiN/Ti/$SiO_2$/Si) including Ti as a common element. In contrast to this method, the present embodiment can measure accurate film thickness of multi-layer films where the films have a common element, whereby the present embodiment is the first to be able to control and administer continuous film forming steps for forming multi-layer films.

The laid-down film structure of TiN/Ti is used as silicide electrodes and protection films for Al wiring.

Silicide electrodes are for thermally reacting with Si at electrode openings to form low resistance electrodes of titanium silicide. The film thickness of the Ti film is very influential on the electrode resistance. A too large film thickness of the Ti film spreads that electrode patterns, and a too small film thickness thereof increases the resistance of the electrodes.

In the protection films for Al wiring, the film thickness of the Ti film influences reliability and electric resistance of the wiring. Therefore, in forming the Ti film by sputtering, it is necessary to reduce the error of the film thickness to some Angstroms by comparing its electric characteristics with results of the Ti film observed by electron microscopes.

Conventionally, there have been no film thickness measuring technique for directly administering of controlling film forming steps, and actually, based on the result of defective characteristics or other characteristics of finished semiconductor devices, causes for the defective characteristics were analyzed after the fact. The present embodiment can measure film thicknesses of the films of such multi-layer film structures simply and accurately. Accordingly, it is possible that films can be formed on monitor samples at the start of a string of film forming steps, and film thicknesses of the films laid in the multi-layer structure can be much improved, whereby measured results can be fed back into the film forming conditions, and techniques for administering or controlling the film forming steps can be much improved.

Thus, the use of the film thickness measuring method according to the present embodiment can efficiently form silicide electrodes and Al wiring of required resistance values.

Titanium Nitride Film: TiN (Density)

Measurement of the film density of a titanium nitride film by the present embodiment will be explained.

The film thickness measurement of titanium nitride film was described above. For titanium nitride film used as a protection film, the density of the film is important for quality of the film. For example, in the case where titanium nitride film is used as the protection film for multi-layer wiring, it has been a risk that $WF_6$ used in burying by CVD tungsten in contact holes for inter-multi-layer wiring may pass through the titanium nitride film used as the protection film, causing release or separation between the titanium film and the aluminium film.

Film density is most suitable as an index of a film, but it has been impossible to measure densities of about several 10 s nm-thickness thin films as the protection films.

By using as initial values, an accurate film thickness measured by the film thickness measuring method according to the present embodiment, a film thickness, a film density and surface roughness can be computed by the fitting method using film thickness, film density and surface roughness as parameters. To make the analysis accurate and quick by this fitting method, it is essential to select a suitable initial value. Conventionally, a design value has been inputted as an initial value. In the present embodiment, however, a measured accurate film thickness can be used as an initial value, whereby the analysis can be accurate and quick. The conventional fitting method has been based on reflectance curves, which suffer from much attenuation. This has made it difficult to see whether or not the fitting results are good. According to the present embodiment, however, the fitting can be conducted based on initially computed oscillation components, and whether or not fitting results are good can be clearly seen.

General fitting methods are described in, e.g., the following papers.

(1) L. G. Paratt, Phys. Rev., 95, 359 (1954)

(2) L. Nevot and P. Croce, Rev. Phys. Appl., 15, 761 (1980)

(3) B. Vidal and P. vincent, Appl. Optics, 23, 1794 (1984)

(4) S. K. Sinha, E. B. Shirota and S. Garoff, Phys. Rev. B, 38, 2297 (1988)

(5) H. Chen and M. Heald, J. Appl. Phys., 66(4), 15, 1793 (1989).

Thus, the present embodiment is the first to have made it practically possible to administer film forming steps, based on film thickness and film density for titanium nitride film, whose film density as well as film thickness greatly influence characteristics of the titanium nitride film.

SiOF Film

An example of the application of the present embodiment to SiOF film forming control will be explained.

Low dielectric SiOF film, which has been developed for the purpose of preventing wiring delay due to parasitic capacitance, is formed by further adding fluorine (F) at the time of forming $SiO_2$ film. Generally SiOF film has the moisture absorption thereof increased by the addition of fluorine, which disadvantageously makes SiOF film less reliable. However, sufficient oxygen is supplied at the time of forming SiOF films to make the films dense, whereby the films do not have increased moisture absorption and are stable.

For example, in the case that SiOF film is formed by CVD using an $SiH_4/N_2O/SiF_4$ mixed gas, the flow rate ratio of the gases is the strongest influence over film density. Furthermore, in the present circumstances, the film forming conditions are so subtle that it is difficult to sufficiently control the film formation.

Then, an accurate film density is measured by the measuring method according to the present embodiment, and this measured result is fed back to film forming conditions, whereby film quality control of SiOF film can be administered with good precision.

Thus, according to the present embodiment, in giving an average reflectance curve $R_{ave}$, data are fitted by using an analysis formula having a term of a product of a power function of an incident angle, which expresses attenuation of a reflectance on a smooth sample surface, an exponent function expressing influence by a rough sample surface, and a constant term expressing a background, so that reflectance characteristics are incorporated in the analysis formula, and the degree of freedom, which has been set arbitrarily conventionally, can be freely and precisely controlled.

As a result, the analysis formula can be universally used in films of different structures, and the measurement can be precise. The measurement can be quicker.

In the present embodiment, as the exponent function term expressing influence of surface roughness, a Debye-Waller roughness was assumed, but attenuation of the reflectance due to the roughness may be accurately expressed by other reduction factors. For example, the expression:

$$\exp(-q \cdot q' \cdot \sigma^2)$$

is applicable as well. In this expression, q and q' are respectively momentum transfer vectors on a substrate and in the substrate, and are expressed by:

$$q=(4\pi/\Lambda)\cdot\sqrt{(n^2-\cos^2\Theta)},$$

and n represents a complex index of refraction.

In the present embodiment, in fitting a curve R to the analysis formula, the method of least squares was used, but other fitting methods may be used as well. For example, the simplex method, the Marcart method, maximum entropy method can be used. In the present embodiment, the analysis formula includes the background constant $B_0$, but when the background component is small, the fitting may be conducted by an analysis formula which does not include a background constant $B_0$.

What is claimed is:

1. A film thickness measuring method comprising the steps of measuring reflectances of X-rays on a film, extracting interference oscillations from the measured X-ray reflectances, and Fourier transforming the interference oscillations to compute a film thickness of the film, an average reflectance being given by fitting the measured X-ray reflectances to an analysis formula including a term of a product of a power function of an incident angle, which expresses attenuation of reflectances on a smooth surface of the film, and an exponent function which expresses influence of roughness of the surface of the film, and a constant term expressing a background added to the product, the interference oscillations being extracted by using the measured X-ray reflectances and the average reflectance.

2. A film thickness measuring method according to claim 1, wherein
the analysis formula is expressed by:

$$I_0(\Theta-\Theta_0)^{-4}\cdot\exp[-(4\pi\sigma/\Lambda\cdot\sin\Theta)^2]+B_0$$

where $I_0$ represents an intensity; $\Theta$, an incident angle of X-rays; $\Theta_0$, an origin offset value for the incident angle $\Theta$; $\sigma$, a root mean square of roughness of the surface of the film; $\Lambda$, a wavelength of the X-rays; and $B_0$, a background constant.

3. A film thickness measuring method according to claim 1, wherein
the roughness of the surface of the film is evaluated based on the root mean square of the roughness of the surface of the film given by fitting the reflectances to the analysis formula.

4. A film thickness measuring method according to claim 2, wherein
the roughness of the surface of the film is evaluated based on the root mean square of the roughness of the surface of the film given by fitting the reflectances to the analysis formula.

5. A film thickness measuring method according to claim 1, wherein
the interference oscillation is given by dividing the measured X-ray reflectances by the average reflectance.

6. A film thickness measuring method according to claim 2, wherein
the interference oscillation is given by dividing the measured X-ray reflectances by the average reflectance.

7. A film thickness measuring method according to claim 1, wherein
the film is a multi-layer film including two or more layers, and
the film thickness is measured by setting incident angles corresponding to positions of layers of the multi-layer film, which are to be measured so that the incident angle is smaller for a layer located on an outer side of the surface of the multi-layer film, and the incident angle is larger for a layer located on an inner side of the multi-layer film.

8. A film thickness measuring method according to claim 2, wherein
the film is a multi-layer film including two or more layers, and
the film thickness is measured by setting incident angles corresponding to positions of layers of the multi-layer film, which are to be measured so that the incident angle is smaller for a layer located on an outer side of the surface of the multi-layer film, and the incident angle is larger for a layer located on an inner side of the multi-layer film.

9. A method for forming a film on a substrate comprising the steps of:
measuring a film thickness of the film by the film thickness measuring method according to claim 1; and
adjusting film forming conditions for the film by using the measured film thickness of the film.

10. A method for forming a film on a substrate comprising the steps of:
measuring a film thickness of the film by the film thickness measuring method according to claim 2; and adjusting film forming conditions for the film by using the measured film thickness of the film.

11. A method for forming a film on a substrate comprising the steps of:
measuring a film thickness of the film by the film thickness measuring method according to claim 1;
computing X-ray reflectances with the measured film thickness of the film as an initial value;
giving a physical amount of at least one of film density and surface and interface roughness of the film by fitting the measured X-ray reflectances to the computed X-ray reflectances; and
adjusting the film forming conditions for the film by using the physical amount of at least one of film thickness, film density and surface and interface roughness of the film.

12. A method for forming a film on a substrate comprising the steps of:
measuring a film thickness of the film by the film thickness measuring method according to claim 2;
computing X-ray reflectances with the measured film thickness of the film as an initial value;
giving a physical amount of at least one of film density and surface and interface roughness of the film by fitting the measured X-ray reflectances to the computed X-ray reflectances; and
adjusting the film forming conditions for the film by using the physical amount of at least one of film thickness, film density and surface and interface roughness of the film.

13. A method for forming a film on a substrate according to claim 11, wherein
by using the physical amount of said at least one of film thickness, film density and surface and interface roughness of the film, at least one parameter of film forming temperature, a gas feed amount, and a gas mixing ratio is adjusted for a processing apparatus for any one of oxidation treatment, nitridation treatment, oxidation/nitridation treatment, sputtering, CVD, electron beam deposition, ion beam deposition, molecular beam deposition and liquid phase growth.

14. A method for forming a film on a substrate according to claim 12, wherein
by using the physical amount of said at least one of film thickness, film density and surface and interface roughness of the film, at least one parameter of film forming temperature, a gas feed amount, and a gas mixing ratio is adjusted for a processing apparatus for any one of oxidation treatment, nitridation treatment, oxidation/nitridation treatment, sputtering, CVD, electron beam deposition, ion beam deposition, molecular beam deposition and liquid phase growth.

15. A method for etching at least a part of a film formed on a substrate comprising the steps of:
measuring a film thickness of the etched film by the film forming method according to claim 1; and
adjusting etching conditions of the film by using the measured film thickness of the film.

16. A method for etching at least a part of a film formed on a substrate comprising the steps of:
measuring a film thickness of the etched film by the film forming method according to claim 2; and
adjusting etching conditions of the film by using the measured film thickness of the film.

* * * * *